United States Patent [19]
Piot et al.

[11] Patent Number: 5,849,278
[45] Date of Patent: Dec. 15, 1998

[54] COSMETIC EYE MAKEUP COMPOSITION COMPRISING A WAX MICRODISPERSION

[75] Inventors: Bertrand Piot, La Garenne Colombes; Myriam Mellul, L'Hay les Roses, both of France

[73] Assignee: L'Oreal, Paris, France

[21] Appl. No.: 458,764

[22] Filed: Jun. 2, 1995

Related U.S. Application Data

[62] Division of Ser. No. 20,073, Feb. 19, 1993, abandoned.

[30] Foreign Application Priority Data

Feb. 21, 1992 [FR] France ................... 92 02059

[51] Int. Cl.⁶ .................................................. A61K 7/032
[52] U.S. Cl. .................... 424/70.7; 424/63; 424/70.11; 424/401; 514/937
[58] Field of Search ............................ 424/401, 63, 70.7, 424/70.11; 514/844, 937, 943

[56] References Cited

U.S. PATENT DOCUMENTS

| | | | |
|---|---|---|---|
| 4,336,246 | 6/1982 | Leon-Pekarek | 424/63 |
| 4,536,405 | 8/1985 | Nara et al. | 424/63 |
| 4,871,536 | 10/1989 | Arraudeau et al. | 424/63 |
| 5,154,916 | 10/1992 | Arraudeau et al. | 424/63 |
| 5,194,260 | 3/1993 | Grollier et al. | 424/401 |
| 5,306,488 | 4/1994 | Vanlerberghe et al. | 424/70.8 |
| 5,389,363 | 2/1995 | Snyder et al. | 424/70.7 |
| 5,431,905 | 7/1995 | Zysman et al. | 424/70.8 |
| 5,618,523 | 4/1997 | Zysman et al. | 424/70.1 |
| 5,620,693 | 4/1997 | Piot et al. | 424/401 |

FOREIGN PATENT DOCUMENTS

| | | |
|---|---|---|
| 394078 | 10/1990 | European Pat. Off. . |
| 2216797 | 10/1989 | United Kingdom . |
| 9112793 | 9/1991 | WIPO . |

OTHER PUBLICATIONS

French Search Report of FR 92 02059.

*Primary Examiner*—Robert H. Harrison
*Attorney, Agent, or Firm*—Nixon & Vanderhye P.C.

[57] ABSTRACT

An eye makeup composition comprises an aqueous dispersion of wax particles, at least one water-soluble film-forming polymer and pigments, the said dispersion being a microdispersion of colloidal wax particles. The composition can be used as viscous mascara compositions which provide a deposit which is smooth and regular and imparts a thickening effect to the eyelashes.

34 Claims, No Drawings

COSMETIC EYE MAKEUP COMPOSITION COMPRISING A WAX MICRODISPERSION

This is a division of application Ser. No. 08/020,073, filed Feb. 19, 1993 now abandoned.

The present invention relates to an eye makeup composition (eyelashes and eyelid borders) whose properties are improved by the presence of microdispersed wax in combination with water-soluble polymers and pigments conventionally employed in this type of composition.

Generally, compositions for use in eyelash makeup, also called "mascaras", or eyelids (called "eyeliners") are made of waxes dispersed using a surfactant in an aqueous phase containing water-soluble polymers and pigments.

By qualitatively and quantitatively selecting the waxes and water-soluble polymers, those skilled in the art know how to formulate mascaras having distinct characteristics.

Thus, it is possible to produce various compositions which, applied to the eyelashes, produce varied effects (elongation or curling or thickening of the eyelashes). Moreover, it is desirable to obtain an eyelash makeup that is "regular", that is the eyelashes have a smooth surface after makeup.

It is difficult to imagine an eyelash makeup having both thickening and regular characteristics, because the thickening effect is achieved with viscous compositions and they are incompatible with the deposit of a regular smooth surface.

It has now been discovered that cosmetic compositions for the eyelashes comprising film-forming water-soluble polymers, in a wax microdispersion containing pigments, produce, in a surprising manner, very interesting makeup characteristics. In effect, they confer a good thickening effect of the eyelashes all while creating a very smooth and regular makeup, despite having a high viscosity, which is necessary for application on the eyelashes using a brush.

In European patent application EP-394078, there is described the use as a cosmetic composition or, hair cosmetic composition support, a fluid composition consisting essentially of a stable wax microdispersion in an aqueous liquid vehicle.

It has been discovered, in a surprising manner, that after the addition of the film-forming polymers and pigments, compositions based on wax microdispersions exhibit remarkable qualities of regular and smooth deposits on the eyelashes.

The present invention thus relates to a cosmetic eye makeup composition comprising an aqueous dispersion of wax particles, at least one film-forming polymer and pigments, and that the said wax dispersion is an aqueous microdispersion of at least one wax.

The said composition generally has a viscosity ranging from 2.5 Pa.s to 25 Pa.s and, for example, between 3.5 and 25 Pa.s, at 25° C.

The wax microdispersions, which are stable dispersions of colloidal wax particles, are known and can be prepared according to known methods; see, for example, "Microemulsions Theory and Practice", L. M. Prince Ed., Academic Press (1977) pages 21–32.

The particles of the wax microdispersion have size lower than 1 $\mu$m, preferably lower than 0.5 $\mu$m. These particles consist essentially of wax or a mixture of waxes. The melting point of the wax or mixture of waxes, is preferably between 50° C. and 100° C. Moreover, the particles of the microdispersion can contain, in minor amounts, pasty or oily fatty additives, one or more surfactants and one or more conventional liposoluble active ingredients, such as those set forth below.

The composition generally contains from 0.1 to 40 percent by weight of wax, in particular 5 to 30 weight percent, and a sufficient amount of at least one emulsifying agent. The amount of the emulsifying agent is that sufficient to obtain a wax microdispersion such as that defined above. This sufficient amount can be determined in each case by routine experimentation.

The waxes are natural substances (animal or vegetable) or synthetic materials solid at ambient temperature (20°–25° C.). They are insoluble in water, soluble in oils and are capable of forming a water repellant film.

With respect to the definition of waxes mention can be made, for example, of P. D. Dorgan, Drug and Cosmetic Industry, December 1983, pp.30–33.

The wax or waxes constituting the wax mixture are selected principally from among Carnauba wax, Candelilla wax and Alfa wax, and their mixtures.

In addition to the waxes mentioned above, the mixture of waxes can also contain one or more of the following waxes or family of waxes:

paraffin wax, ozokerite, vegetable waxes such as olive tree wax, rice wax, hydrogenated jojoba wax or absolute waxes of flowers such as the essential wax of cassis flower sold by Bertin (France);

animal waxes such as beeswax, or modified beeswax (cerabellina);

other waxes or primary waxy materials: marine waxes such as that sold by Sophim under the name "M82", natural or synthetic ceramides or polyethylene waxes.

The vegetable waxes of Carnauba (extract of Copernica Cerifera), of Candelilla (extract of Euphobies Cerifera and Pedilantus pavonis) and of Alfa (extract of Stipa tenacissima), are commercial products.

The ceramides are the principal lipid constituents of the intercorneocytal spaces of the stratum corneum. They are described, in particular, by Downing in Science, 1982, Vol. 18, p. 1261–2. Synthetic analogs are also known, such as ceramides HO3, sold by Cosmind.

In the mixture of waxes, Carnauba wax and/or Candelilla wax and/or Alfa wax represent at least 20 percent, and preferably at least 50 percent by weight relative to the total weight of the mixture of waxes.

The wax or mixture of waxes can contain, in addition to the waxes mentioned above, at least one other wax and/or at least one oil, it being understood that the mixture of waxes and optionally oil have an end melting point greater than 50° C.

The mixture of waxes can then be combined with one or more fatty additives (oily or pasty). Mention can be made, in a non-restrictive manner, of:

vegetable oils such as turnsol oil, jojoba oil, etc.;

mineral oils such as paraffin oil, fluid silicone oils having a viscosity ranging principally between 0.65 and 100,000 centistokes (or between $0.65 \times 10^{-4}$ and 10 $m^2.s^{-1}$, preferably between 5 and 5,000 centistokes (or between $5 \times 10^{-4}$ and $5 \times 10^{-1} m^2.s^{-1}$), fluorinated oils and waxes, petrolatum and lanolin.

The mixture of oil(s) and/or pasty fatty additives can represent up to 30 percent (preferably more than 10 percent) of the weight of wax.

It is also possible to introduce into the microparticulate waxy phase some liposoluble active ingredients.

When present, the liposoluble ingredient represents 30 present at the maximum and preferably 10 percent at the maximum, of the weight of the microparticles.

As liposoluble ingredient(s) mention can be made, for example, of:

U.V. filters, liposoluble vitamins, anti-inflammatory agents such as β-glycyrrethinic acid and liposoluble vegetable extracts.

The use of surfactants as emulsifying agents in the preparation of wax microdispersions is known. The production of the microdispersion can be carried out using anionic, cationic and/or nonionic surfactants, in a known manner.

The percentage of surfactant(s) in the final composition generally ranges from 0.01 to about 25 percent and in particular from 0.1 to 10 percent.

The wax(es)/emulsifying agent(s) weight ratio can vary, for example, in the range 1 to 30 and principally 2 to 10.

The anionic surfactants employed are principally salts of fatty acids (for example alkaline salts or organic salts such as amine salts), the said fatty acids having, for example, from 12 to 16 carbon atoms and being able to have a double bond as in the case of oleic acid, alkaline salts or organic base salts of alkyl-sulfuric and alkyl sulfonic acid having 12 to 18 carbon atoms, alkyl-arylsulfonic acids whose alkyl chain contains from 6 to 18 carbon atoms, the aryl group being, for example, a phenyl group. They are also ether-sulfates, in particular the sulfatation products of fatty alcohols and polyalkoxylated alkyl phenols in which the aliphatic chain contains from 6 to 20 carbon atoms and the polyalkoxylated chain from 1 to 30 oxyalkylene units, in particular oxyethylene, oxypropylene or oxybutylene.

All these anionic surfactants are well known and many of them are commercial products.

The nonionic surfactants are principally polyalkoxylated and/or polyglycerolated surfactants. They are principally polyalkoxylated and/or polyglycerolated fatty acids or amides of fatty acids; polyalkoxylated and/or polyglycerolated fatty alcohols or alkylphenols; polyalkoxylated and/or polyglycerolated esters of fatty acids and polyols; polyalkoxylated and/or polyglycerolated 1,2- or 1,3-alkanediols or alkenediols; polyalkoxylated and/or polyglycerolated alkylethers of 1,2- or 1,3-alkanediols or alkenediols. For example, the fatty acids or alcohols, optionally unsaturated, have 12–24 carbon atoms, the alkyl chain of the alkylphenols has 6 to 16 carbon atoms, the alkanediols or alkenediols have from 9 to 24 carbon atoms, the alkyl of the alkylethers has from 4 to 20 carbon atoms, and the number of oxyalkylene units or of (CH$_2$CHOHCH$_2$O) units can range from 2 to 40.

The polyalkoxylated nonionic derivatives are principally polyoxyethylenated, optionally polyoxypropylenated derivatives.

The polyalkoxylated fatty acids are commercial products, principally those sold under the trade name "NYRJ®" by Atlas.

The polyoxyethylenated esters of fatty acids and polyols for which the polyol is sorbitol are known products (Polysorbate and products sold under the trade name "TWEEN®" by Atlas). When the polyol is glycerol, products sold by Goldschmidt under the trade name "TAGAT®" can be used.

The polyoxyethylenated fatty alcohols are commercial products, principally those sold under the mark "BRIJ®" by Atlas.

The polyglycerolated fatty alcohols, polyglycerolated alkanediols or alkenediols, or the polyglycerolated alkylethers of alkanediols or alkenediols can be prepared, for example, according to the processes disclosed in French patents 1.477.048; 2.025,681; 2.091.516 and 2.465.780 or according to analogous procedures.

The polyglycerolated fatty acids or amides of fatty acids are principally disclosed in French patent 1.484.723 or are, again, commercial products such as those sold under the trade name "PLUROL®" by Gattefosse, or "DREWPOL®" by the Stefan Company, or "DECAGLYN®", by Nikko Chemical.

Other useful nonionic surfactants are, for example:

triglycerol alkylcarbamates having the general formula:

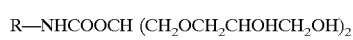

R—NHCOOCH (CH$_2$OCH$_2$CHOHCH$_2$OH)$_2$ wherein R represents a saturated or unsaturated alkyl group having 10–20 carbon atoms. These compounds are described in EP patent 0420761;

oxyethylenated or propoxylated derivatives of lanolin alcohols, lanolin fatty acids, or mixtures thereof.

Such surfactants are sold by Amerchol under the trade name "SOLULAN®".

The cationic surfactants are principally quaternary ammonium derivatives such as ARQUAD 16–50®, ARQUAD 18–50®, ARQUAD 18–50®, ARQUAD T-50®, ARQUAD 2C-75®, ETHOQUAD C/12® and ETHOQUAD 0/12®.

The use of nonionic surfactants is preferred.

It is also possible to prepare wax microdispersions by using commercial mixtures of self-emulsifiable waxes containing the wax and surfactants.

There can be employed, for example, the wax sold under the trade name "CIRE AUTO LUSTRANTE OFR®" by Tiscco, which contains Carnauba and paraffin waxes, in combination with nonionic emulsifying agents, or the self-emulsifiable wax sold under the trade name "CERAX A.O. 28/B®" by La Ceresine, which contains Alfa wax in combination with a nonionic emulsifying agent. These commercial mixtures permit the preparation of wax microdispersions by the addition of water in accordance with the process described above.

There can also be employed ready-to-use wax microdispersions, available commercially as the "SERIE SL SLIPAID®" products of Daniel Products Company, or even "AQUACER®" products of Cerachemie.

The wax microdispersions are dilutable with water without interfering with the stability of the microdispersion. Consequently they can be provided in the form of concentrated compositions the proportions of the ingredients of which can be adjusted to a desired value by the simple addition of water.

The film-forming polymers useful in the composition of the invention can be anionic, cationic, nonionic or amphoteric polymers.

These film-forming polymers, as well as their use in eye makeup compositions, are known.

Described in greater detail below, as an illustration, are certain film-forming polymers useful in the compositions according to the invention. There can be employed synthetic polymers or polymers of natural origin, chemically modified or not modified. Mention can principally be made of cationic polymers which are polymers of the polyamine, polyaminopolyamide or quaternary polyammonium type in which the amine or ammonium group is a part of the polymer chain or is linked to it; they generally have a molecular weight ranging from 500 to 3,000,000.

As useful cationic film-forming polymers, mention can be made, for example, of:

(1) vinylpyrrolidone/dialkylaminoalkyl acrylate or methacrylate copolymers (quaternized or not), such as those sold under the trade names "GAFQUAT®" by GAF Corp., as for example, "copolymer 845", "GAFQUAT 734 or 735®", described in greater detail in French patents 2393537 and 2077141;

(2) cellulose ether derivatives having quaternary ammonium groups such as those described in French patent 1492597 and principally polymers sold under the designations "JR®", such as "JR 125®, JR 400®, JR 30M®, and LR®, such as LR 400® and LR®" by Union Carbide Corp., cationic cellulose derivatives such as "CELQUAT L200® and CELQUAT H 100®", which-are sold by National Starch or those sold by Akzo under the designation "LEOGARD GP®";

(3) cationic polysaccharides described in U.S. Pat. Nos. 3,589,978 and 4,031,307, and in particular "JAQUAR C135®" sold by Meyhall;

(4) cationic polymers containing alternate units of the formula : —A—Z—, wherein A represents a radical containing two amine functions and the Z groups represent at least one bivalent radical, such as the polymers described in French patents 2162025 and 2280361;

(5) cyclopolymers such as the homo- and copolymers of dimethyl diallylammonium chloride sold under the designation "MERQUAT®" by Merck. These polymers are described in French patents 2080759 and 2194406;

(6) the quaternized vinylimidazolium-vinylpyrrolidone copolymers such as those sold under the trade name "LUVIQUAT FC or HM®" by BASF;

The anionic film-forming polymers are polymers having anionic groups, in particular carboxylic and/or sulfonic groups.

The preferred anionic polymers employed in the compositions of the invention are selected principally from among:

(1) the homo- or copolymers of acrylic or methacrylic acids or their salts and their esters and in particular the products sold under the trade names "VERSICOL F®" or "VERSICOL K®" by Allied Colloid, "ULTRAHOLD 8®" by Ciba-Geigy, the copolymers of acrylic acid and acrylamide sold under the form of their sodium salt under the designation "RETEN®" by Hercules, sodium polymethacrylate sold under the designation "DARVAN No 7®" by Vanderbilt, the sodium salts of polyhydroxycarboxylic acids, sold under the trade name "HYDAGEN F®" by Henkel;

(2) copolymers derived from crotonic acid and their esters such as those described, for example, in French 1222944; 1580545; 2265781; 2265782; 1564110 and 2439798;

(3) polymers or copolymers derived from maleic, fumaric or itaconic acids or anhydrides with vinylic or phenylvinylic or acrylic derivatives, these polymers being able to be esterified.

Such polymers are described in particular in U.S. Pat. Nos. 2,047,398; 2,723,248, French patent 2102113 and British 839805.

Among these polymers, mention can be made of the polymers sold under the designations "GANTREZ®" by the GAF Corporation or "EMA®" by Monsanto. Polymers also belonging in this class are the copolymers of maleic, citraconic or itaconic anhydrides and an allylic or methallylic ester having optionally an acrylamide or methacrylamide group in their chain, monoesterified or monoamidified, described in French patents 2350834 and 2357241;

(4) useful polymers having sulfonic groups in accordance with the invention are selected principally from among:
salts of polystyrene sulfonic acid such as those described principally in French patent 2198719,
polyacrylamide sulfonic salts such as those mentioned in U.S. Pat. No. 4128631,
polyester salts such as those sold under the trade name "POLYMER EASTMAN AQ®" by Kodak,
sulfonic keratins such as those described in French patent 2529214.

The amphoteric film-forming polymers useful in the compositions of the invention are principally polymers having M and M' units statistically distributed in the polymer chain, where M represents at least one unit derived from a monomer having at least one basic nitrogen atom and M' represents at least one unit derived from an acid monomer having one or more carboxylic or sulfonic groups, or even M and M' can represent groups derived from zwitterionic monomers of carboxybetaine. M and M' can also represent a cationic polymer chain having secondary, tertiary or quaternary amine groups, in which at least one of the amino groups has a carboxylic or sulfonic group linked by the intermediary or a hydrocarbon chain, or even M and M' are part of a chain of a polymer having an ethylene alpha-, beta dicarboxylic unit of which one of the carboxylic groups has reacted with a polyamine having one or more primary or secondary amine groups.

Mention can be made, for example, of:

(1) polymers or copolymers having units derived:
 (a) from at least one monomer selected from among the acrylamides or methacrylamides, substituted at the nitrogen by an alkyl radical,
 (b) from at least one acid monomer containing one or more reactive carboxylic groups, and
 (c) from at least one basic comonomer such as esters having a primary, secondary, tertiary or quaternary amine substituent of acrylic and methacrylic acids and the quaternization products of dimethylaminoethyl methacrylate with dimethyl or diethyl sulfate. As compounds representative of this class mention can be made of "AMPHOMER®" sold by Natural Starch;

(2) polymers derived from chitosan such as described, for example, in French patent 2137684 or U.S. Pat. No. 3829376;

(3) copolymers of diallyl dialkyl (C1–C4) ammonium/acrylic acid such as the product sold under the trade name "MERQUAT 280" by Merck which is a copolymer of diallyl dimethyl ammonium chloride/acrylic acid.

The nonionic film-forming polymers useful in the compositions of the invention are principally:

(1) the homo- and/or copolymers of vinylpyrrolidone such as the polyvinylpyrrolidone/vinyl acetate copolymer sold under the trade name "PVP/PVA S-630®" by GAF, or the trade name "LUVISKOL®" by BASF;

(2) the nonionic vinylic homopolymers or copolymers such as polyvinyl alcohol sold under the trade name "MOWIOL 4088®" by Hoechst;

(3) poly β-alanines described more particular in BE-20851 patent;

(4) derivatives of polyaspartic acid such as those described in French patent 2403076;

(5) or even polyglycols such as polyethylene glycols.

Mention can also be made of the family of polyurethanes in solution or anionic, cationic or nonionic dispersion, as well as the family of proteins, quaternized or not, among which are keratin derivatives (such as "KERASOL®" sold by Croda).

Among the film-forming polymers useful in the compositions of the invention mention can also be made of cellulosic and saccharidic polymers such as hydroxymethyl cellulose, carboxymethyl cellulose, hydroxybutyl cellulose, hydroxypropyl cellulose, and more particularly, hydroxyethyl cellulose, in particular the products sold under the trade name "NATROSOL®" by Hercules or "CELLOSIZE®" by Union Carbide, methylhydroxypropyl cellulose, in particular the products sold under the trade name "METHOCEL®" by Dow Chemical or heterobiopolysaccharides such as for example, xanthan gums sold under the marks "KELTROL®" and "KELZAN®" by Kelco, "RHODOPOL®" and "RHODIGEL®" by Rhone Poulenc, or "ACTIGUM®" by Ceca/Satia, gum arabic, guar gum, Karoya gum, alginates and carraghenates, hyaluronic acid and its derivatives.

The film-forming polymers are selected preferably from among hydroxyethyl cellulose, gum arabic, polyvinylpyrrolidone, cationic cellulose derivatives, sodium polymethacrylate and keratin hydrolyzates.

The film-forming polymers are present in the composition generally in an amount ranging from 0.1 to 25 percent by weight and preferably from 0.2 to 15 percent by weight.

The composition can contain one or more polymers in solution in the aqueous phase of the preparation.

The composition according to the invention contains at least one pigment in an amount ranging principally up to 20 percent and preferably between 0.1 and 20 percent by weight relative to the total weight of the composition, depending upon the coloration and intensity of coloration that is desired. The use of pigments in such compositions is known. The notion of pigment includes non-colored particulate charges.

The useful pigments are selected principally from among mineral pigments, organic pigments and nacreous pigments.

Among the mineral pigments mention can be made, for example, of:
  titanium dioxide (rutile or anatase), optionally surface-treated and listed in the Color Index under the reference CI 77891;
  black, yellow, red and brown iron oxides, listed under the references CI 77499, 77492, 77491;
  manganese violet (CI 77742);
  ultramarine blue (CI 77007);
  chrome oxide (CI 77288);
  chrome hydrate (CI 77289); and
  ferric blue (CI 77510).

Among the organic pigments, mention can be made in particular, of pigments certified in the United States of America by the Food and Drug Administration under the designations:
  D&C Red No. 19 (CI 45170);
  D&C Red No. 9 (CI 15585);
  D&C Red No. 30 (CI 73360);
  D&C Red No. 3 (CI 45430);
  D&C Red No. 21 (CI 45380);
  D&C Red No. 27 (CI 45410);
  D&C Red No. 13 (CI 15630);
  D&C Red No. 7 (CI 15850-1);
  D&C Red No. 6 (CI 15850-2);
  D&C Red No. 36 (CI 12085);
  D&C Orange No. 10 (CI 45425);
  D&C Orange No. 4 (CI 15510);
  D&C Orange No. 5 (CI 45370);
  D&C Yellow No. 6 (CI 15985);
  D&C Yellow No. 5 (CI 19140); as well as
  carbon black (CI 77266); and
  natural or synthetic melanin;
  lakes based on cochenille carmin (CI 75470);

The nacreous pigments can be selected principally from among:
  white nacreous pigments, such as mica covered with titanium oxide, bismuth oxychloride and boron nitride;
  colored nacreous pigments, such as titanium mica with iron oxides, titanium mica with ferric blue, or chromium oxide, titanium mica with an organic pigment of the type mentioned above, as well as those based on bismuth oxychloride;
  coated pigments such as those obtained with the pigments mentioned above the surface of which has been treated with various substances such as, for example, amino acids, silicones, metallic salts or collagen.

Moreover, the composition according to the invention can optionally contain one or more particulate charges conventionally employed in this type of composition such as: talc which is hydrated magnesium silicate, used in the form of particles generally having a size less than 40 micrometers; micas, which are aluminosilicates of varied compositions provided in the form of flakes generally having a size ranging from 2 to 200 micrometers, preferably from 5 to 70 micrometers, and a thickness ranging from 0.1 to 5 micrometers, preferably from 0.2 to 3 micrometers. These micas can be of natural origin (for example, muscovite, margarite, roscoelithe, lipidolithe, biotite) or of synthetic origin; starch, in particular rice starch; kaolin, which is a hydrated aluminum silicate and which is provided in the form of particles of isotrope form having a size generally less than 30 micrometers; zinc and titanium oxides, generally employed in the form of particles having a size not exceeding a few micrometers; calcium carbonate or magnesium carbonate or hydrocarbonate; microcrystalline cellulose; powders of synthetic polymers, such as polyethylene, polyesters (for example, polyethylene isophthalate or terephthalate), polyamides (for example nylon powders), the "teflons" and silicone powders.

In a general manner, the colored or non-colored charges, can be coated by substances such as amino acids, silicones, metallic soaps or collagen, or be submitted to any other treatment so as to modify the surface state.

The cosmetic compositions according to the invention can also contain one or more conventional adjuvants such as thickening agents, perfumes, preservatives, alkalinizing or acidifying agents, texture agents, spreading agents, plasticizers as well as water-soluble active ingredients conventionally employed in preparations for the eyelashes.

In the compositions of the invention, the film-forming polymers can exercise a thickening effect. To adjust the viscosity of the composition to the desired value additional conventional thickening agents can be added.

The additional thickening agent(s) when they are present, have for an effect to stabilize the dispersion pigments and thus avoid decantation of these pigments, and to impart to the final composition the necessary consistency favoring the production of a sheathing with a thickening of the eyelash.

Thickening of the formulations can also be accomplished by the film-forming polymer or by a combination of the film-forming polymer and a texturing agent selected, for example, from among colloidal silicas, bentones or polyethylene glycol distearate having 150 ethylene oxide units.

Other known thickening agents can be employed and are selected, for example, from among polyacrylic acids crosslinked by a polyfunctional agent such as the products sold under the designation "CARBOPOLS®" by Goodrich, such as "CARBOPOLS 910, 934, 934P, 940, 941, 980, 1342®", natural or modified clays such as the "LAPONITES®" of Laporte or "VEEGUM®" of Vanderbilt or polyurethanes.

With or without additional thickening agents, the viscosity of the preparations according to the invention range from 2.5 to 35 Pa.s. and preferably from 3.5 to 25 Pa.s at about 25° C., for example when it is measured with a Contraves viscosimeter (rotation time—10 minutes at 200 rpm).

The spreading additives can be fluorinated derivatives such as those sold by 3M under the name "FLUORAD®", or copolyol dimethicone surfactants having a high HLB available from Dow Corning, Goldschmidt, etc.

As plasticizers mention can be made, for example, of the PEGs (polyethylene glycols) of low molecular mass, glycerine and panthenol.

The compositions according to the invention are obtained by forming hot a microemulsion. More precisely, these compositions are obtained by a process principally characterized by the fact that the wax and the emulsifying agent are heated to a temperature greater than the melting temperature of the wax and not greater than 100° C., optionally in the presence of a portion of the water, until the wax is completely melted; that water, or the remainder of water is progressively added, the water being heated to a temperature at least equal to the said temperature employed to melt the wax, while stirring, until a wax microemulsion is formed in a continuous aqueous phase, and then permitting the whole to cool to ambient temperature. A stable wax microdispersion is thus obtained.

The process is carried out with stirring and a sufficient amount of surfactant is employed so that the size of the wax microparticles is less than 1,000 nm, preferably 500 nm.

The liposoluble ingredients, for example, ceramides, are generally added with the wax prior to the formation of the microdispersion.

The water-soluble ingredients can be added in the water used to produce the microdispersion, or in the finally obtained wax microdispersion.

Also, the secondary ingredients optionally present in the composition are added either to the starting products or to the finished composition.

The compositions of the invention are applied either to the eyelashes, or to the edge of the eyelids, in a known manner, using a brush or a pencil.

The invention also relates to the use of an aqueous wax microdispersion, in combination with at least one water-soluble film-forming polymer and pigments, in the preparation of a composition for eye makeup.

The composition obtained can exhibit the other characteristics which have been described above.

The invention also relates to an eye makeup process characterized by the fact that there is applied to the eyelashes or to the edge of the eyelids, a composition such as previously defined.

The following examples illustrate the invention.

EXAMPLES OF PREPARING WAX MICRODISPERSION

Examples A and B

|  | A | B |
|---|---|---|
| Carnauba wax | 40.0 g | 30.0 g |
| Polyoxyethylenated glycerol monostearate (30 ethylene oxide units) sold under the trade name TAGAT S ® by Goldschmidt | 10.0 g | 7.5 g |
| Methyl parahydroxybenzoate | 0.2 g | 0.2 g |
| Water, sufficient amount for | 100.0 g | 100.0 g |

The mixture of wax(es), preservatives and surfactant(s) is heated to 90° C. (generally 10° C. above the melting point of the wax or mixture of waxes and fatty bodies) while homogenizing with moderate stirring.

While continuing to stir, water heated to 90° C. is incorporated therein.

The resulting microemulsion is cooled to ambient temperature and forms a microdispersion of particles based on wax(es).

Average diameter of the wax particles: A=184 nm, B=155 nm.

Example C

| | |
|---|---|
| Carnauba wax | 30.0 g |
| Lanolin alcohol and mixture of polyoxyethylenated fatty alcohols (25 ethylene oxide units) sold under the trade name SOLULAN 25 ® by Amerchol | 7.5 g |
| Methyl parahydroxybenzoate | 0.2 g |
| Water, sufficient amount for | 100.0 g |

The microdispersion is obtained by proceeding as described in Examples A and B.

Average diameter of wax particles: 99 nm "x EO" means: oxyethylenated with x moles of ethylene oxide.

Example D

| | |
|---|---|
| Carnauba wax | 22.5 g |
| Paraffin wax | 7.5 g |
| Beeswax | 10.4 g |
| Methyl parahydroxybenzoate | 0.2 g |
| Polyoxyethylenated glycerol monostearate (30 ethylene oxide units), sold under the trade name TAGAT S ® by Goldschmidt | 7.5 g |
| Water, sufficient amount for | 100.0 g |

The microdispersion is obtained by proceeding as described in Examples A and B.

Average size of wax particles: 202 nm

Example E

| | |
|---|---|
| Carnauba wax | 22.5 g |
| 1-(2'-F-hexylethylthio)-3-(2"-ethylhexyloxy) propane-2-ol | 7.5 g |
| TAGAT S ® | 7.5 g |
| Methyl parahydroxybenzoate | 0.2 g |
| Water, sufficient amount for | 100.0 g |

The microdispersion is obtained by proceeding as described in Examples A and B.

Average diameter of wax particles: 230 nm The fluorinated oil 1-(2'-F-hexylethylthio)-3-(2"-ethylhexyloxy)-2-propane-2-ol is prepared in the following manner:

At a temperature of 25° C., with stirring and under a nitrogen stream there are added to 152 g of 2-F-hexylethanethiol, 3.6 g of a methanolic solution of sodium methylate (about 30%—5.54 meq g$^{-1}$) in a period of one minute.

The mixture is heated to 70° C. and the methanol present in the medium is evaporated under a vacuum.

2-ethylhexylglycidyl ether (74.4 g) is then added dropwise over a one hour period. The temperature of the mixture is maintained between 60° and 70° C. during the course of the epoxide addition.

At the end of the addition the temperature is reduced to 25° C.

The mixture is neutralized using 20 ml of 1N HCl.

The 1-(2'-F-hexylethylthio)-3-(2"-ethylhexyloxy)-2-propanol is separated by distillation: Boiling point=141° C./66.5 Pa.

175 g (77%) of a colorless translucent oil are obtained.

Example F

| | |
|---|---|
| Carnauba wax | 18 g |
| 1-(2'-F-octlethylthio)-2-hexanol | 12 g |
| TAGAT S ® | 7.5 g |
| Methyl parahydroxybenzoate | 0.2 g |
| Water, sufficient amount for | 100 g |

The microdispersion is obtained by proceeding as described in Examples A and B.

Average diameter of the wax particles: 195 nm.

The fluorinated wax 1-(2'-F-octylethylthio)-2-hexanol is prepared in the following manner:

In accordance with a procedure analogous to that described in Example E, there are condensed, in a one-hour period, 30 g (0.3 mole) of 1,2-epoxyhexane with 144 g (0.3 mole) of 2-F-octylethanethiol in the presence of 2.7 g of a methanolic solution of sodium methylate (5.65 meq. g$^{-1}$).

At the end of the reaction, the mixture is neutralized with 15 ml of 1N HCl.

After distillation (154° C./133 Pa) 115 g of an amorphous white solid which is 1-(2'-F-octylethylthio)-2-hexanol are obtained.

Yield=67% ; Melting point=45° C.

EXAMPLES OF EYE MAKEUP COMPOSITIONS

Eye makeup compositions are prepared by mixing with the above microdispersion the below indicated ingredients. The amounts are expressed in grams.

Example 1

| | |
|---|---|
| Wax microdispersion according to Example A | 93.75 |
| Black iron oxide | 6.00 |
| Hydroxyethyl cellulose, sold under the trade name CELLOSIZE QP 4400 H" by Amerchol | 0.25 |

Example 2

| | |
|---|---|
| Wax microdispersion according to Example A | 89.7 |
| Black iron oxide | 6.0 |
| Hydroxyethyl cellulose, sold under the trade name CELLOSIZE QP 4400 H ® by Amerchol | 1.0 |
| Gum arabic | 1.0 |
| Water | 2.3 |

Examples 3, 4 and 5

| | 3 | 4 | 5 |
|---|---|---|---|
| Wax microdispersion according to Example A | 50.0 | 89.0 | 87.0 |
| Polyvinylpyrrolidone, sold under under the trade name LUVISKOL K90 POWDER ® by BASF | 6.0 | 4.0 | 6.0 |
| Black iron oxide | 6.0 | 6.0 | 6.0 |
| Gum arabic | | 1.0 | |
| Water | 38.0 | | |
| Fluorinated surfactant, sold under the trade name FLUORAD FC 143 ® by 3M | | | 0.3 |
| Shininess of composition | 77 | 60 | 77 |

Example 6 and 7

| | 6 | 7 |
|---|---|---|
| Carnauba wax | 15.8 | 23.7 |
| Paraffin wax | 1.7 | 2.6 |
| Polyoxyethylenated glycerol monostearate (30 EO) sold under the trade name TAGAT S ® by Goldschmidt | 4.4 | 6.6 |
| Polyvinylpyrrolidone, sold under the trade name LUVISKOL K90 POWDER ® by BASF | 6.0 | 6.0 |
| Black iron oxide | 6.0 | 6.0 |
| Methyl parahydroxybenzoate | 0.1 | 0.1 |
| Water, sufficient amount for | 100.0 | 100.0 |

Example 8

| | |
|---|---|
| Microdispersion of Carnauba wax, sold under the trade name AQUACER 608 ® by Cerachemie | 93.0 |
| Black iron oxide | 6.0 |
| Hydroxyethyl cellulose | 1.0 |
| Shininess of the composition: | 24 |

Example 9

| | |
|---|---|
| Wax microdispersion according to Example C | 88.0 |
| Black iron oxide | 6.0 |
| Gum arabic | 2.0 |
| Polyvinylpyrrolidone | 4.0 |

Example 10

| | |
|---|---|
| Wax microdispersion according to Example A | 74.0 |
| Gum arabic | 1.0 |
| Colloidal silica, sold under the trade name COK 84 ® by Degussa | 4.0 |
| Glycerine | 15.0 |
| Black iron oxide | 6.0 |

Examples 11 to 14

|  |  | 11 | 12 | 13 | 14 |
|---|---|---|---|---|---|
| Phase I | Stearic acid |  |  | 8 |  |
|  | Beeswax |  |  | 6 |  |
|  | Glycerol stearate | 1.9 |  |  |  |
|  | TAGAT S ® | 5.15 |  |  |  |
|  | Carnauba wax | 28.4 |  | 5 |  |
|  | Paraffin |  |  | 6 |  |
|  | Wax microdispersion according to Example B |  | 91.46 |  | 85.5 |
| Phase II | Panthenol |  |  | 1.5 | 5.0 |
|  | Gum arabic | 3.0 | 3.0 | 6.0 | 3.0 |
|  | Hydroxyethyl cellulose | 0.5 | 0.5 | 1.0 | 0.5 |
|  | PVP* | 1.0 | 1.0 |  | 1.0 |
|  | LEOGARD GPA ® | 2.0 | 2.0 |  | 1.0 |
|  | Titanium oxide | 2.0 | 2.0 |  |  |
|  | Black iron oxide |  |  | 5.0 | 5.0 |
|  | NaOH | 0.4 | 0.4 |  |  |
|  | Triethanolamine |  |  | 4.2 |  |
|  | Preservative | sufficient | sufficient | sufficient | sufficient |
|  | Water, sufficient amount for | 100.0 |  |  | 100.0 |

*LUVISKOL K90 POWDER ®

Preparations 12 and 14 are produced in accordance with the operating procedures described above for Example 1. Preparations 11 and 13 are produced by mixing phase 1 heated to 85° C. Phase II is prepared by heating water to 85° C. and adding to it the polymers. The emulsion is produced by adding phase II to phase I at a temperature of 82° C. Then the titanium oxide or iron oxide is added. The temperature is progressively reduced while continuing vigorous stirring of the paste.

Comparison of Examples 11 and 12

Preparation 12 applied to the eyelashes exhibits an appearance clearly more smooth and more shiny than composition 11.

Preparations 11 and 12 are deposited on a glass plate with an applicator so as to produce a homogeneous deposit. Once dried, the films thus produced have a thickness of about 100 μm. This corresponds to the thickness deposited on average on the eyelashes during makeup.

The mascara film 12 is very clearly more shiny and more smooth than the film of mascara 11.

The state of the surface was studied with a profilometer laser. This study has confirmed the very clearly more smooth appearance of the film 12.

Comparison of Examples 13 and 14

Eyelashes have been made up with the formulations of Examples 13 and 14, then electronic microscopic photos of the eyelashes were made.

Composition 13 (size of wax particles>1000 nm) represents the state of the art while composition 14 represents a composition of microdispersed waxes according to the invention.

Visual observation of the makeup results has shown that mascara 14 applied on the eyelashes exhibits an appearance indeed more smooth and regular than mascara 13.

Electronic microscope photos have confirmed these observations.

Operating Procedure for Producing the Compositions of Examples 1–14, 21 and 22

Operating Procedure I (Compositions 1–5, 8 and 9)

The process is effected by dilution of the starting wax microdispersion (2 steps).

At ambient temperature, the polymer is incorporated into the wax microdispersion with stirring with the amount of water necessary (optionally) to obtain a homogeneous preparation. Then, the pigments are dispersed therein.

The resulting formulation can be pulverized.

Composition of Example 5 is obtained by the addition of fluorinated surfactants followed by pulverization.

Operating Procedure II (Compositions 6 and 7)

The preparation of the makeup composition is effected in a hot stage.

Waxes, surfactants and preservatives are melted and mixed together at 90° C.

The pigments are dispersed in the lipophile phase at about 90° C.

The polymer is dissolved in water cold. The aqueous phase is then heated to 90° C. and poured into the lipophile phase with stirring, all while maintaining the temperature at about 90° C. until homogeneous. Then the composition is cooled and optionally passed through a grinder.

Operating procedure III (Composition 10)

At the cold, the pigments and silica are dispersed in a wax microdispersion.

The polymer and hydrophilic additive are added with mild stirring until a homogenous preparation is produced. The preparation can then be pulverized.

Measurement of shininess

The preparation is spread (100 to 300 μm thick) on a glass plate. After 24 hours of drying, the shininess is measured with a Microgloss (BYK) brilliance meter under an angle of 85°.

Examples 15–20

| Wax microdispersion according to: | 15 | 16 | 17 | 18 | 19 | 20 |
|---|---|---|---|---|---|---|
| Example B | 88.4 | 89.5 | 90.3 | 87.5 | 85.5 |  |
| Example D |  |  |  |  |  | 86.2 |
| Wheat germ oil | 1 |  |  |  |  |  |
| Silicone oil (PDMS) |  |  |  | 0.5 |  |  |
| Paraffin oil |  |  |  |  | 1.5 |  |
| PVP | 2 | 1 |  | 2.5 |  | 1 |
| Luviquat FC 905 ® (BASF) |  |  |  |  | 3 |  |
| Leogard GP ® (Akzo) |  |  | 0.2 | 3 |  |  |
| Darvan 7 ® (Vanderbilt) |  |  | 2 |  |  |  |
| Gum arabic | 1.5 | 3 |  |  |  | 5 |
| Hydroxyethyl cellulose |  | 0.5 | 1.5 |  |  | 0.8 |
| Kerasol (Croda) |  |  |  |  | 1.5 |  |
| CARBOPOL 1342 ® (Goodrich) | 0.6 |  |  |  |  |  |
| Carbon black |  |  | 3 |  |  |  |
| Black iron oxide | 6 | 5 |  | 1 | 1 | 5 |
| Brown iron oxide |  |  |  | 4 |  |  |
| Ultramarine blue |  | 1 |  |  | 4 | 1 |
| Talc |  |  |  | 1 |  |  |
| ORGASOL 2002 |  |  | 2 |  |  |  |
| NATCOS ® (ATO) |  |  |  |  |  |  |
| α-bisabolol |  |  |  |  | 0.5 |  |
| Panthenol |  |  | 1 |  | 5 | 1 |
| Triethanolamine | 0.5 |  |  |  |  |  |
| Preservatives | qs | qs | qs | qs | qs | qs |

The operating procedure is that of Example 1. All the compositions of these Examples have a viscosity ranging from 4 to 25 Pa.s.

All these preparations applied to the eyelashes give a thickening effect while imparting to them a very striking smooth and regular appearance. Moreover, Examples 16, 18 and 20 correspond to mascaras having a very high degree of shininess.

Silicone oil PDMS is that sold under the trade name DOW CORNING 200 FLUID by Dow Corning.

PVP: Polyvinyl pyrrolidone sold under the trade name LUVISKOL K90 POWDER® by BASF.

LUVIQUAT FC 905®: copolymer of methyl vinylimidazolium chloride and vinylpyrrolidone (95/5), 40% solution of active material in water sold by BASF.

LEOGARD GP®: Hydroxyethyl cellulose crosslinked with epichlorohydrin and quaternized by trimethylamine, sold by Akzo. DARVAN 7®: Sodium polymethacrylate, 25% solution of active material in water, sold by Vanderbilt.

KERASOL®: Stabilized keratin hydrolyzate, sold by Croda.

CARBOPOL 1342®: Crosslinked acrylate/$C_{10}C_{30}$ alkyl acrylate polymer sold by Goodrich.

ORGASOL 2002 NATCOS®: Nylon 12 (CTFA name), powder sold by Ato.

Example 21

| | |
|---|---|
| Microdispersion of Example E | 90 g |
| Hydroxyethyl cellulose | 1 g |
| Gum arabic | 1.5 g |
| Polyvinyl alcohol, sold under the trade name RHODOVIOL 4/125 ® by Rhone Poulenc | 0.5 g |
| Black iron oxide | 5.0 g |
| Ultramarine blue | 2.0 g |
| Preservative, sufficient amount | |

Example 22

This composition is analogous to that of Example 21 except that the microdispersion of Example F is employed rather than that of Example E.

We claim:

1. An eye makeup composition comprising an aqueous dispersion of wax particles, at least one water-soluble film-forming polymer, 0.01 to 25 percent by weight of at least one surfactant based on the total weight of said composition, and a pigment, the said dispersion being an aqueous microdispersion of at least one wax and said composition having a viscosity ranging from 3.5 Pa.s to 25 Pa.s at 25° C.

2. The composition of claim 1 wherein said wax particles have a size less than 500 nm.

3. The composition of claim 1 wherein said wax particles are present in an amount ranging from 0.1 to 40 weight percent.

4. The composition of claim 1 wherein said wax particles are present in an amount ranging from 5 to 30 weight percent.

5. The composition of claim 1 wherein said wax has a melting point ranging from 50° to 100° C.

6. The composition of claim 1 wherein said wax comprises a vegetable wax selected from the group consisting of Carnauba wax, Candellila wax and Alfa wax.

7. The composition of claim 6 wherein said wax comprises at least 20 percent by weight of said vegetable wax based on the total weight of said wax.

8. The composition of claim 6 wherein said wax comprises at least 50 percent by weight of said vegetable wax based on the total weight of said wax.

9. The composition of claim 6 wherein said wax contains at least one other wax or at least one oil or both, it being understood that the mixture of waxes and the mixture of waxes and the mixture of waxes and oil has a final melting point greater than 50° C.

10. The composition of claim 9 wherein said other wax or oil or both represents at most 30 weight percent relative to the total weight of said wax.

11. The composition of claim 9 wherein said other wax or oil or both represents at most 10 weight percent relative to the total weight of said wax.

12. The composition of claim 1 wherein said film-forming polymer is present in an amount ranging from 0.2 to 15 percent by weight.

13. The composition of claim 1 which also includes a thickening agent or a texturing agent in an amount effective to adjust the viscosity of said composition.

14. The composition of claim 1 wherein said pigment is present in an amount ranging from 0.1 to 20 percent by weight.

15. The eye makeup composition of claim 1 wherein said wax microdispersion contains at least one liposoluble active ingredient present in an amount at the maximum of 30 percent by weight based on the weight of said wax.

16. The eye makeup composition of claim 1 wherein said wax microdispersion contains at least one liposoluble active ingredient present in an amount at the maximum of 10 percent by weight based on the weight of said wax.

17. The eye makeup composition of claim 1 which also includes at least one surfactant in an amount ranging from 0.1 to 10 percent by weight based on the total weight of said composition.

18. The eye makeup composition of claim 1 wherein said film-forming polymer is selected from the group consisting of hydroxyethyl cellulose, gum arabic, polyvinylpyrrolidone, cationic cellulose derivative, sodium polymethacrylate and keratin hydrolyzate.

19. An eye makeup composition comprising an aqueous dispersion of wax particles, at least one water-soluble film-forming polymer, 0.01 to 25 percent by weight of at least one surfactant based on the total weight of said composition, and a pigment, said wax particles (1) being present in an amount ranging from 0.1 to 40 weight percent, (2) having a melting point ranging from 50° to 100° C. and (3) having a size less than 1,000 nm, said film-forming polymer being present in an amount ranging from 0.1 to 25 percent by weight and said pigment being present in an amount ranging from 0.1 to 20 weight percent; and said composition having a viscosity ranging from 2.5 Pa.s to 35 Pa.s at 25° C.

20. The composition of claim 19 wherein said wax microdispersion contains at least one liposoluble active ingredient present in an amount at the maximum of 30 percent by weight based on the weight of said wax.

21. The composition of claim 19 wherein said wax microdispersion contains at least one liposoluble active ingredient present in an amount at the maximum of 10 percent by weight based on the weight of said wax.

22. The composition of claim 19 which also includes at least one surfactant in an amount ranging from 0.1 to 10 percent by weight based on the total weight of said composition.

23. The composition of claim 19 wherein said film-forming polymer is selected from the group consisting of hydroxyethyl cellulose, gum arabic, polyvinylpyrrolidone, cationic cellulose derivative, sodium polymethacrylate and keratin hydrolyzate.

24. The eye makeup composition of claim 19 wherein said wax particles have a size less than 500 nm.

25. The eye makeup composition of claim 19 wherein said wax particles are present in an amount ranging from 5 to 30 weight percent.

26. The eye makeup composition of claim 19 wherein said wax comprises a vegetable wax selected from the group consisting of Carnauba wax, Candellila wax and Alfa wax.

27. The eye makeup composition of claim 26 wherein said wax comprises at least 20 percent by weight of said vegetable wax based on the total weight of said wax.

28. The eye makeup composition of claim 26 wherein said wax comprises at least 50 percent by weight of said vegetable wax based on the total weight of said wax.

29. The eye makeup composition of claim 26 wherein said wax contains at least one other wax or at least one oil, or both, it being understood that the mixture of waxes and the mixture of waxes and oil has a final melting point greater than 50° C.

30. The eye makeup composition of claim 29 wherein said other wax or oil or both represents at most 30 weight percent relative to the total weight of said wax.

31. The eye makeup composition of claim 29 wherein said other wax or oil or both represents at most 10 weight percent relative to the total weight of said wax.

32. The eye makeup composition of claim 19 which also includes a thickening agent or a texturing agent in an amount effective to adjust the viscosity of said composition.

33. An eye makeup composition comprising an aqueous dispersion of wax particles, at least one water-soluble film-forming polymer, 0.01 to 25 percent by weight of at least one surfactant based on the total weight of said composition, and a pigment, the said dispersion being an aqueous microdispersion of at least one wax and said composition having a viscosity ranging from 3.5 Pa.s to 25 Pa.s at 25° C., said film-forming polymer being present in an amount ranging from 0.1 to 25 percent by weight.

34. An eye makeup composition comprising an aqueous dispersion of wax particles, at least one water-soluble film-forming polymer, 0.01 to 25 percent by weight of at least one surfactant based on the total weight of said composition, and a pigment, said wax particles (1) being present in an amount ranging from 0.1 to 40 weight percent, (2) having a melting point ranging from 50° to 100° C. and (3) having a size less than 1,000 nm, said film-forming polymer being present in an amount ranging from 0.2 to 15 percent by weight and said pigment being present in an amount ranging from 0.1 to 20 weight percent; and said composition having a viscosity ranging from 2.5 Pa.s to 35 Pa.s at 25° C.

* * * * *